US006689720B2

(12) United States Patent
Woznica et al.

(10) Patent No.: US 6,689,720 B2
(45) Date of Patent: Feb. 10, 2004

(54) HIGH-PH OIL BASED ADJUVANT BLEND FOR ENHANCING EFFICACY OF PESTICIDES

(75) Inventors: Zenon J. Woznica, Fargo, ND (US); Calvin Messersmith, Fargo, ND (US); John Nalewaja, Fargo, ND (US)

(73) Assignee: NDSU-Research Foundation, Fargo, ND (US)

( * ) Notice: Subject to any disclaimer, the term of this patent is extended or adjusted under 35 U.S.C. 154(b) by 45 days.

(21) Appl. No.: 10/034,841

(22) Filed: Dec. 27, 2001

(65) Prior Publication Data

US 2003/0104947 A1 Jun. 5, 2003

Related U.S. Application Data

(63) Continuation-in-part of application No. 09/992,475, filed on Nov. 14, 2001.

(51) Int. Cl.$^7$ .................. A01N 25/22; A01N 43/70; A01N 47/38; B01F 17/00
(52) U.S. Cl. .................. 504/362; 504/211; 504/212; 504/213; 504/214; 504/215; 504/234; 504/235; 504/253; 504/363; 516/204; 516/199; 71/54; 71/58; 71/59; 71/61
(58) Field of Search .................. 504/302, 363, 504/213, 215, 211, 212, 214, 234, 235, 253; 516/204, 198; 71/54, 58, 59, 61

(56) References Cited

U.S. PATENT DOCUMENTS

| | | |
|---|---|---|
| 4,017,641 A | 4/1977 | DiGiulio ................ 424/365 |
| 4,092,273 A | 5/1978 | Inamorato et al. ........ 252/548 |
| 4,125,398 A | 11/1978 | Roth ..................... 71/115 |
| 4,227,911 A | 10/1980 | Leonard et al. ............. 71/77 |
| 4,749,404 A | 6/1988 | Parsons ................... 71/92 |
| 4,954,279 A | 9/1990 | Ma et al. ................ 252/70 |
| 4,971,630 A | 11/1990 | Skaptason ............... 71/117 |
| 5,078,782 A | 1/1992 | Nielsen et al. ............ 71/100 |
| 5,118,338 A | 6/1992 | Moller .................... 71/86 |
| 5,266,553 A | 11/1993 | Champion et al. ......... 504/206 |
| 5,341,932 A | 8/1994 | Chen et al. ............. 206/524.7 |
| 5,346,704 A | 9/1994 | Lajoie .................. 424/717 |
| 5,356,861 A | 10/1994 | Gednalski et al. ......... 504/206 |
| 5,407,899 A | 4/1995 | Howell .................. 504/152 |
| 5,409,885 A | 4/1995 | Derian et al. ............ 504/116 |
| 5,411,932 A | 5/1995 | Yoshida et al. ........... 504/132 |
| 5,430,005 A | 7/1995 | Kassebaum et al. ........ 504/206 |
| 5,468,715 A | 11/1995 | Joseph et al. ............ 504/101 |
| 5,563,112 A | 10/1996 | Barnes III .............. 504/125 |
| 5,658,855 A | 8/1997 | Nalewaja et al. .......... 504/214 |
| 5,871,666 A | 2/1999 | Gross ................... 252/312 |
| 5,919,733 A | 7/1999 | Sedun et al. ............. 504/320 |
| RE37,313 E | 8/2001 | Roberts .................. 424/405 |
| 6,488,780 B2 * | 12/2002 | Cauwet-Martin ........... 134/42 |

FOREIGN PATENT DOCUMENTS

WO   98/22087   * 5/1998

OTHER PUBLICATIONS

Green et al., "Surfactant Structure and Concentration Strongly Affect Rimsulfuron Activity", Weed Technology, vol. 7, pp. 633–640, 1993.
Holloway, "Adjuvants for Foliage–Applied Agrochemicals: The Need for More Science not Serendipity?" $4^{th}$ International Symposium on Adjuvants for Agrochemicals, Melbourne, Australia, pp. 167–175, Oct. 3–6, 1995.
"Imazaquin–Imazethapyr", WSSA Herbicide Handbook, $7^{th}$ Ed., pp. 166, 1994.
Miller et al., "Barban–Aqueous Nitrogen Combinations for Wild Oat(*Avena fatua*) Control", Weed Science, vol. 26, Issue 4, pp. 344–348, Jul. 1978.
Nalewaja et al., "Salts and Surfactants Influence Nicosulfuron Activity", Weed Technology, vol. 9, pp. 587–593, 1995.
Nalewaja et al., Spray Carrier Salts Affect Herbicide Toxicity to Kochia (*Kochia scoparia*), Weed Technology, vol. 7, pp. 154–158, 1993.
"Nicosulfron", WSSA Herbicide Handbook, $7^{th}$ Ed., pp. 216–217, 1994.
North Dakota State University Weed Control Research entitled, "Summary of 2000 Weed Control Experiments", 2000.
"Picioram–Primisulfron", WSSA Herbicide Handbook, $7^{th}$ Ed., 1994.
Renegade Specimen label and Material Safety Data sheet.
Wanamarta et al., "Overcoming Antagonistic Effects of Na–Bentazon on Sethoxydim Absorption", Weed Technology, vol. 7, pp. 322–325, 1993.

* cited by examiner

*Primary Examiner*—S. Mark Clardy
(74) *Attorney, Agent, or Firm*—Fitch, Even, Tabin & Flannery

(57) ABSTRACT

The present invention relates to a homogenous adjuvant blend for use in spray carriers containing herbicides. The homogenous adjuvant blend includes an oil, a pH adjuster, and nonionic surfactants.

30 Claims, No Drawings

HIGH-PH OIL BASED ADJUVANT BLEND FOR ENHANCING EFFICACY OF PESTICIDES

This application is a continuation-in-part application of U.S. Ser. No. 09/992,475, filed Nov. 14, 2001, which is incorporated herein in its entirety by reference.

STATEMENT OF GOVERNMENT RIGHTS

The U.S. Government has a paid-up license in this invention and the right in limited circumstances to require the patent owner to license others on reasonable terms as provided for by the terms of Grant Nos. 97-34361-3960, 98-34361-6831 and 99-34361-8432 awarded by the U.S. Department of Agriculture.

This invention relates to a homogenous adjuvant blend for use in spray carriers containing herbicides, which are used to control weeds or other undesired vegetation. More specifically, the homogenous adjuvant blend of the invention includes a blend of oil, a pH adjuster, and nonionic surfactants.

BACKGROUND

Herbicides used in controlling weeds or undesired vegetation in agriculture may be applied by postemergence spraying of a herbicide on the crop. The spray carrier for the herbicide is usually a water-based adjuvant mixture containing an effective amount of known herbicide. Adjuvants are commonly added to herbicidal spray mixtures to enhance postemergence weed control and/or to reduce spray drift during herbicide applications.

Postemergence weed control applications are enhanced when the spray containing the herbicide is retained on the weed surface. To obtain sufficient retention of the herbicide on the weed surface, many "sticker" compositions or agents, including methylated vegetable oils or mineral based oils and surface active agents (surfactants), are used as adjuvants. These adjuvants act to improve adherence of the herbicide on weeds, help retain droplets of the spray solution on the plant, and improve penetration of the herbicide into the plant.

In addition to spray retention by the weed, other additives in the form of liquid nitrogen based fertilizer solutions have been found, for example, to enhance the control of wild oats by herbicides such as barban. Miller et al., *Weed Science*, 1978, Vol. 4, pp. 344–348. Recently surfactants have been combined with liquid fertilizers (usually 28% nitrogen, comprising a mixture of about 50% ammonium nitrate and about 50% urea). The results however are variable depending on surfactants used and nitrogen fertilizer employed. It was found that certain salts and surfactants influence nicosulfuron herbicide activity. Nalewaja et al., *Weed Technology*, 1995, Vol. 9, pp. 587–593.

Some acidic additives have previously been used which are designed to lower pH and enhance the acidity of the spray carrier water formulation, which was believed to both benefit herbicide adsorption and also to prevent alkaline hydrolysis of certain insecticides. Acids and buffering agents are sometimes also used to reduce antagonism from alkaline salts found in the spray carrier water (U.S. Pat. Nos. 5,393,791; 5,178,795 and RE No. 37,313).

It has been noted that adjuvants differ greatly in herbicide enhancement depending on the specific surfactant and the herbicide used. In some cases, adjuvant can result in decreased performance. Halloway, *4th International Symposium on Adjuvants for Agrochemicals,* 1995, FR. & Bulletin, No. 193.

Adjuvants which are a three component system including an alkaline amine pH regulator, a non-ionic surfactant, and a neutral ammonium salt, such as ammonium nitrate, ammonium chloride, and ammonium sulfate, are described in U.S. Pat. No. 5,658,855. All three components were required to provide the desired phytotoxicity.

One concern over the use of adjuvants is not only in its ability to enhance herbicide efficacy but in its ability to maintain product stability. Many adjuvants may be blended with herbicides and water that are available at the site of blending. In some cases, the available blending water may contain minerals or other substances that result in formation of precipitates and general instability of the composition.

SUMMARY

The present invention relates to homogenous and stable adjuvant blends for use in a spray carrier of postemergence herbicides applied as an aqueous spray solution to areas infested with undesired weeds or plants to control the same. The adjuvant compositions of the present invention are stable and act synergistically at low rates to increase spray retention, and provide lipophilic and hydrophilic environments in the spray deposits that enhance leaf penetration and efficacy of herbicides. The adjuvant of the present invention is provided as a single stable formulation that reduces the need to add separate components to a spray tank mix.

The adjuvant of the present invention is a multi-component composition that includes an oil, a pH adjuster for adjusting the pH to an alkaline range, and nonionic surfactants. In one aspect of the invention, the oil may be a petroleum oil. In this aspect, the adjuvant blend may only contain a petroleum oil, or alternatively, may further include an oil or mixture of oils selected from the group consisting of vegetable oils, methylated, ethylated and butylated seed oil, fatty acids, partially saponified fatty acids, and mixtures thereof. In the aspect of the invention where the adjuvant blend contains only petroleum oil, the blend contains from about 30 to about 70 weight percent petroleum oil, based on the weight of the adjuvant blend. In the aspect of the invention where the adjuvant blend contains petroleum oil and a second oil, the blend contains from about 1 to about 69 weight percent petroleum oil, based on the weight of the adjuvant blend, and from about 1 to about 69 weight percent, based on the weight of the adjuvant blend, of a second oil or mixture of second oils.

In another aspect of the invention, the blend includes an oil selected from the group consisting of petroleum oil, vegetable oils, methylated, ethylated and butylated seed oil, fatty acids, partially saponified fatty acids, and mixtures thereof. In this aspect of the invention, the blend contains from about 30 to about 70 weight percent oil or mixture of oils, based on the weight of the adjuvant blend.

The second component of the homogenous adjuvant blend of the present invention is a pH adjuster. The pH adjuster of the invention is effective for providing an alkaline pH of above about 7 up to about 10 for the final spray solution that is applied to the plants. The pH adjuster may be organic and/or inorganic. Examples of of pH adjusters include ammonium hydroxide, potassium hydroxide, sodium hydroxide, triethanolamine, primary amino alcohols, and mixtures thereof. In an important aspect of the invention, the pH adjuster component is about 0.01 weight percent to about 10 weight percent of the adjuvant composition, preferably about 5 percent by weight of the adjuvant composition.

The next components of the homogenous adjuvant blend is a nonionic surfactant. Nonionic surfactants useful in the present invention include linear alcohol ethoxylates, secondary alcohol ethoxylates, block copolymers of ethylene and propylene oxide, and mixtures thereof. The adjuvant blend contains from about 30 to about 70 weight percent nonionic surfactant, based on the weight of the adjuvant blend.

In another aspect, about 0.5 to about 1 percent of the homogenous adjuvant blend of the present invention is blended with water and with an effective amount of herbicide to provide a postemergence herbicidal spray composition, which is applied for weed control purposes. In this aspect of the invention, the herbicidal spray composition includes about 95 to about 99 percent water, about 0.001 to about 4 percent herbicide, and about 0.5 to about 1 percent of the adjuvant of the present invention, based on the weight of the herbicidal spray composition. The herbicide is customarily added to the water at the recommended label amount; for example, herbicide in an amount from about 0.1 to about 4 ounces per acre of the herbicide active ingredients is a typical application rate.

DETAILED DESCRIPTION

The homogenous adjuvant blend of the present invention is a multi-component mixture including an oil, pH adjuster, and nonionic surfactant. The percentage of each ingredient is blended to provide a homogenous and stable formulation. As used herein a "homogenous and stable" formulation means that all components of the adjuvant composition when mixed together form a clear, continuous blend that does not separate during storage at temperatures between 32° F. and 122° F. for at least about 180 days.

In an important aspect of the invention, the homogenous adjuvant blend increases the efficacy of certain herbicides. The ingredients, acting synergistically, produce a low application rate formulation. In practice, similar ingredients are added to the spray mixture separately, at much higher rates. Using the adjuvant blend components in one spray formulation, at a rate of about 0.5 to about 1% of the spray mixture volume, provides a convenient and time-saving combination for farmers. The present invention increases spray retention, prevents pesticide antagonism from salts in the spray water, and enhances leaf penetration.

Oil

The adjuvant composition of the present invention includes an oil. In alternative aspects of the invention, the oil may be petroleum oil, a mixture of petroleum oil and a second oil, or an oil or mixture of oils selected from the group consisting of petroleum oil, vegetable oils, methylated, ethylated and butylated seed oil, fatty acids, partially saponified fatty acids, and mixtures thereof.

As used herein, petroleum oil means oil derived from petroleum that contains a mixture of hydrocarbons, broadly classified as paraffins, napthenes, aromatics, or other unsaturates, or combinations thereof. Paraffinic oil, which typically has a paraffinic carbon content greater than 60%, is the most useful petroleum oil in the present invention.

Vegetable oils useful in the present invention include any oil from canola oil, cottonseed oil, corn oil, linseed oil, palm oil, rapeseed oil, safflower oil, soybean oil, and sunflower oil.

Modified vegetable oils useful in the present invention include methylated, ethylated, and butylated seed oils from all major crops. Modified methylated, ethylated, and butylated vegetable oils in general increase efficacy of many herbicides more than petroleum or non-modified vegetable oils. Modified vegetable oils mainly increase the herbicide penetration and are especially effective with many herbicides when they are applied in mixtures with nitrogen fertilizers (e.g., with liquid ammonium nitrate-urea fertilizer).

As used herein "fatty acids" include caproic acid, caprylic acid, erucic acid, lauric acid, linolenic acid, linoleic acid, mysteric acid, oleic acid, palmitic acid, stearic acid, and mixtures thereof. Fatty acids are obtained by hydrolysis of animal and vegetable oils (triglycerides). As a result of this reaction, glycerine and mixed fatty acids are obtained. Fatty acids (e.g. stearic acid, palmitic acid, lauric acid, mysteric acid, caprylic acid, caproic acid, palmitic acid) differ in degree of saturation and length of carbon (C) chain (usually between C6 and C22, with the vast majority in C18). Companies that supply free fatty acids include Akzo Nobel Chemicals (Chicago, Ill.) and Uniquema (Wilmington, Del.).

As used herein "partially saponified fatty acids" include ammonium, potassium or sodium salts of caproic acid, caprylic acid, erucic acid, lauric acid, linolenic acid, linoleic acid, mysteric acid, oleic acid, palmitic acid, stearic acid, and mixtures thereof. Salts of fatty acids, e.g., potassium or sodium salts, are called "soaps" and are obtained by the process of saponification (fatty acids are treated with strong bases, e.g., sodium or potassium hydroxide). The term "partially saponified" means that only a certain percentage of fatty acids are converted to salts (soap) and the final product is a mixture of free fatty acid(s) and salts of free fatty acids (soaps).

pH Adjuster

In an important aspect of the invention, the pH adjuster of the invention provides an alkaline pH of the final spray solution of above about 7 up to about 10, which is effective to increase solubility of the herbicide active ingredient. This is particularly important when used with herbicides from the sulfonylurea group (e.g., foramsulfuron, nicosulfuron, rimulfuron, primisulfuron).

Alkaline compounds are especially important in the present invention. Examples of pH adjusters include ammonium hydroxide, triethanolamine, primary amino alcohols (e.g., 2-amino-1-butanol, 2-amino-2-methyl-1-propanol, 2-amino-2-methyl-1,3-propanediol, 2-amino-2-methyl-1-propanol, 2-dimethylamino-2-methyl-1-propanol, 2-amino-2-ethyl-1,3-propanediol, tris(hydroxymethyl) aminomethane, 2-dimethylamino-2-methyl-1-propanol), and mixtures thereof. The pH adjuster component should be about 0.01 to about 10 percent by weight of the adjuvant composition, and in an important aspect preferably is ammonium hydroxide at about 5 percent by weight of the adjuvant composition.

Nonionic Surfactants

In an important aspect of the invention, the adjuvant composition includes nonionic surfactants. The nonionic surfactants may include linear alcohol ethoxylates, secondary alcohol ethoxylates, block copolymers of ethylene and propylene, and mixtures thereof.

As used herein "linear alcohol ethoxylates" include surfactants such as Alfaonic, (810-40, HLB 8; 810-60, HLB 12; 1012-40, HLB 8; 1012-60, HLB 12; 1012-80, HLB 16), products of Condea Vista Company.

As used herein "secondary alcohol ethoxylates" refer to surfactatns such as Tergitols, (15-S-3, HLB 8.3; 15-S-5, HLB 10.5; 15-S-7, HLB 12.4; 15-S-9, HLB 13.3; 15-S-12, HLB 14.7; 15-S-15, HLB 15.6; 15-S-20, HLB 16.4; 15-S-30, HLB 17.5; 15-S-40, HLB 18.0), products of Union Carbide.

The nonionic surfactants may be block copolymer surfactants, having a high HLB (Hydrophilic-Lipophilic Balance) broadly above about 14 to about 18, or a low HLB broadly above 1 to about 10. In the aspect of the invention where block copolymers are used, each block copolymer surfactant is about 20 to about 40 percent by weight of the adjuvant composition, and preferably each block copolymer surfactant is about 30 percent by weight of the adjuvant composition.

High HLB indicates that a surfactant molecule is relatively more water than oil soluble. One system of obtaining HLB is by dividing the percentage of the water soluble portion of the surfactant molecule by 5. HLB values for surfactants are usually provided by the surfactant supplier and are also available from McCutcheon's Emulsifiers & Detergents, McCutcheon Division, McCutcheon Publishing Co., 175 Rock Road, Glen Rock, N.J. 07452. High HLBs of the present invention are considered hydrophilic. In an important aspect of the invention, certain water soluble herbicides are enhanced more by high than low HLB surfactants.

Examples of suitable block copolymer surfactants having a high HLB are Pluronics, block copolymers of propylene oxide and ethylene oxide, products of BASF Corp., (L64, HLB 15; L84, HLB 14; P85, HLB 16, P104, HLB 13; P105, HLB 15). Examples of suitable non-ionic surfactants having a low HLB are Pluronics, block copolymers of propylene oxide and ethylene oxide, products of BASF Corp., (L62, HLB 7; L92, HLB 6; P123, HLB 8).

Application of Homogenous Adjuvant Blend

The homogenous adjuvant blend is customarily formulated and sold in two and one half (2½) gallon or larger containers. The adjuvant blend is used to make up the spray mixture, which also includes spray water (about 95% to about 99%) and a herbicidally effective amount of a postemergence herbicide, customarily 2% or less by weight of the aqueous spray mixture. The herbicide is customarily added to the water at the recommended label amount; for example, in an amount effective for providing an application rate of from about 0.1 to about 4 ounces per acre of the herbicide active ingredient. In this aspect of the invention, the spray applied to the plants is typically from about 0.5 to 1 weight percent adjuvant, preferably 0.5 weight percent, from about 0.001 to about 4 weight percent, preferably about 0.001 to about 2 weight percent herbicide, with the remainder of the spray being water.

The adjuvant blend of the present invention is effective for use with herbicides that require addition of oil based adjuvants, or surfactants and for which solubility in water is increased by high pH, which includes sulfonylurea and weak acid herbicides. The oils and surfactants of the present invention act to improve spray retention and herbicide absorption by weeds and the high pH maintains the herbicide in a more available chemical form for absorption.

Preferably, the herbicides employed in this invention are selected from the group consisting of:

Nicosulfuron (sold under the tradename Accent) which is the compound [[[[(4,6-dimethoxy-2-pyrimidinyl)amino]carbonyl]amino]sulfonyl-N,N-dimethyl-3-pyridine carboxy amide;

Rimsulfuron (sold under the trade name Matrix) which is the compound N-[[(4,6-dimethoxy-2-pyrimidinyl)amino]carbonyl]-3-(ethylsulfonyl)-2-pyridinesulfonamide);

Imazethapyr (sold under the trade name Pursuit), 2-[4,5-dihydro-4-methyl-4-(1-methylethyl)-5-oxo-1H-imidazol-2-yl]-5-ethyl-3-pyridinecarboxylic acid;

Primisulfuron (sold under the trade name Beacon), 2-[[[[[4,6-bis(difluoromethoxy)-2-pyrimidinyl]amino]carbonyl]amino]sulfonyl]benzoic acid;

Foramsulfuron, 2-[[[[(4,6-dimethoxy-2-pyrimidinyl)amino]carbonyl]amino]sulfonyl]-4-(formylamino)-N,N-dimethylbenzamide;

Mesotrione, (sold under the trade name Callisto), 2-[4-(methylsulfonyl)-2-nitrobenzoyl-1,3-cyclohexanedione;

Quizalofop, (sold under the trade name Assure II), 2-[4-[(6-chloro-2-quinoxalinyl)oxy]phenoxy]propanoic acid;

Clethodim, (sold under the trade name Select), (E,E)-2-[1-[[(3-chloro-2-propenyl)oxy]imino]propyl]-5-[2-(ethylthio)propyl]-3-hyroxy-2-cyclohexen-1-on;

Flucarbazone (sold under the trade name Everest), 4,5-dihydro-3-methoxy-4-methyl-5-oxo-N-[[2-(trifluorometh oxy)phenyl]sulfonyl]-1H-1,2,4-triazole-1-carboxamide;

Atrazine (sold under various trade names), 6-chloro-N-ethyl-N'-(1-methylethyl)-1,3,5-triazine-2,4-diamine, and mixtures thereof.

In an important aspect, the invention provides postemergence herbicidal aqueous spray compositions that include:

(A) an oil in an amount of from about 30 to about 70 percent by weight of the adjuvant blend;

(B) a pH adjuster in an amount effective for providing an alkaline pH of above about 7 to about 10 of the final herbicidal aqueous spray mixture;

(C) a nonionic surfactant;

(D) a herbicide; and (E) additional water to make up the final spray solution.

EXAMPLES

Example 1

Adjuvant Compositions

Three example homogenous adjuvant blends Composition 1, 2, and 3) were prepared as follows. Ammonium hydroxide was added into methylated canola oil (in Composition 1 and Composition 2) or into petroleum oil (in Composition 3) and pre-stirred. Next, Pluronic L 62.RTM (Composition 1), Pluronic L 62.RTM and Tergitol 15-S-5.RTM (Composition 2) or Tergitol 15-S-5.RTM and Tergitol 15-S-9.RTM (Composition 3) were added, while slowly stirring, until the formulations were homogenous, clear, without separation. The formulations were stable for a storage time of from 1 to at least 180 days at temperature ranges between 32 and 122° F.

| Component | Composition 1 % weight/weight |
|---|---|
| Methylated canola oil | 55 |
| Ammonium hydroxide | 5 |
| Pluronic L 62.RTM | 40 |

Pluronic L 62.RTM is a block copolymer nonionic surfactant from BASF Corp.; Tergitol 15-S-5.RTM and Tergitol 15-S-9.RTM are secondary alcohol ethoxylate surfactants, both from Union Carbide Corp.

| Component | Composition 2 % weight/weight |
|---|---|
| Methylated canola oil | 55 |
| Ammonium hydroxide | 5 |
| Pluronic L 62.RTM | 20 |
| Tergitol 15-S-9.RTM | 20 |

Pluronic L 62.RTM is a block copolymer nonionic surfactant from BASF Corp.; Tergitol 15-S-9.RTM is a secondary alcohol ethoxylate surfactant from Union Carbide Corp.

| Component | Composition 3 % weight/weight |
|---|---|
| Petroleum oil | 50 |
| Ammonium hydroxide | 5 |
| Tergitol 15-S-5.RTM | 20 |
| Tergitol 15-S-9.RTM | 25 |

Tergitol 15-S-5.RTM and Tergitol 15-S-9.RTM are secondary alcohol ethoxylate surfactants, both from Union Carbide Corp.

Example 2

Efficacy

The adjuvants Activator 90.RTM, Scoil.RTM, 28%N, Composition 1, and Composition 2 were added into water (volume per volume concentration are shown in TABLE 1) with nicosulfuron (0.2 oz/A) to prepare the final aqueous spray mixture applied at 8.5 gal/A on 3–4 leaf stage large crabgrass. TABLE 1 includes the results of assessment made 3 WAT (weeks after treatment). Visible injury rating is on a scale of 0 to 100% with 0% representing no visible injury and 100% complete kill.

Efficacy of nicosulfuron increased as methylated vegetable oil (Scoil.RTM) concentration increased from 0.5 to 1%. However, Composition 1 and Composition 2 adjuvants of present invention applied at 0.5% provided higher nicosulfuron efficacy than Scoil.RTM applied at 0.5 and 1% and equal than Scoil.RTM applied at 1% plus 28%N nitrogen fertilizer at 2%.

TABLE 1

Large crabgrass control 3 WAT with nicosulfuron (0.2 oz/A) as influenced by adjuvants (greenhouse tests)

| Adjuvant | % visible injury injury | % fresh weight reduction |
|---|---|---|
| None | 31 | 57 |
| Activator 90.RTM 0.5% | 39 | 64 |
| Activator 90.RTM 0.5% + 28%N 2% | 53 | 74 |
| Scoil.RTM 0.5% | 50 | 70 |
| Scoil.RTM 0.5 + 28%N 2% | 78 | 85 |
| Scoil.RTM 1% | 70 | 76 |
| Scoil.RTM 1% + 28%N 2% | 86 | 93 |
| Composition 1 0.5% | 92 | 92 |
| Composition 1 0.5% + 28%N 2% | 89 | 91 |
| Composition 2 0.5% | 87 | 87 |

TABLE 1-continued

Large crabgrass control 3 WAT with nicosulfuron (0.2 oz/A) as influenced by adjuvants (greenhouse tests)

| Adjuvant | % visible injury injury | % fresh weight reduction |
|---|---|---|
| Composition 2 0.5% + 28%N 2% | 97 | 92 |
| LSD (0.05) | 4 | 5 |

Activator 90.RTM is a nonionic surfactant of alkylpolyoxyethylene ethers and free fatty acids from Loveland Industries. Scoil.RTM is methylated vegetable oil from AGSCO Inc.; 28%N is a liquid nitrogen fertilizer comprising urea and ammonium nitrate; Composition 1 is an experimental homogenous adjuvant that refers to the present invention consisting of methylated canola oil (55%), ammonium hydroxide (5%), and Pluronic L 62.RTM block copolymer nonionic surfactant (40%) from BASF Corp. Composition 2 is an experimental homogenous adjuvant that refers to the present invention consisting of methylated canola oil (55%), ammonium hydroxide (5%), Pluronic L 62.RTM block copolymer nonionic surfactants (20%) from BASF Corp., and Tergitol 15-S-9.RTM secondary alcohol ethoxylate surfactant from Union Carbide Corp.

The adjuvants Activator 90.RTM, Scoil.RTM, Prime Oil.RTM, Hi-Per-Oil.RTM, Composition 1, and Composition 2 were added into water (concentrations based on volume per volume or pt/A are shown in TABLE 2) with nicosulfuron (0.2 oz/A) to prepare the final aqueous spray mixture applied at 8.5 gal/A on 3-leaf stage large crabgrass. TABLE 2 includes the results of assessment made 3 WAT (weeks after treatment).

Composition 1 and Composition 2 adjuvants of present invention applied at the reduced concentrations of 0.5% and at 0.75 pt/A provided better nicosulfuron efficacy than methylated seed oil Scoil.RTM applied at concentrations of 1% and 1.5 pt/A, or petroleum oils Prime Oil.RTM at 2 pt/A and Hi-Per-Oil.RTM at 1 pt/A.

TABLE 2

Large crabgrass control 3 WAT with nicosulfuron (0.2 oz/A) as influenced by adjuvants (greenhouse tests)

| Adjuvant | % visible injury | % fresh weight reduction |
|---|---|---|
| Activator 90 0.5% | 31 | 17 |
| Scoil.RTM 1% | 61 | 62 |
| Scoil.RTM 1.5 pt/A | 60 | 71 |
| Prime Oil.RTM 2 pt/A | 41 | 49 |
| Hi-Per-Oil.RTM 1 pt/A | 32 | 25 |
| Composition 1 0.5% | 95 | 92 |
| Composition 1 0.75 pt/A% | 90 | 91 |
| Composition 2 0.5% | 90 | 90 |
| Composition 2 0.75 pt/A | 98 | 92 |
| LSD (0.05) | 2 | 10 |

Activator 90.RTM is a nonionic surfactant of alkylpolyoxyethylene ethers and free fatty acids from Loveland Industries. Scoil.RTM is a methylated vegetable oil from AGSCO Inc.; Prime Oil.RTM is a petroleum oil from Agriliance. Hi-Per-Oil.RTM is a petroleum oil from Agriliance. Composition 1 is an experimental homogenous adjuvant that refers to the present invention consisting of methylated canola oil (55%), ammonium hydroxide (5%), and Pluronic L 62 block copolymer nonionic surfactant (40%)

from BASF Corp. Composition 2 is an experimental homogenous adjuvant that refers to the present invention consisting of methylated canola oil (55%), ammonium hydroxide (5%), Pluronic L 62.RTM block copolymer nonionic surfactant (20%) from BASF Corp., and Tergitol 15-S-9.RTM secondary alcohol ethoxylate surfactant (20%) from Union Carbide Corp.

The results of field tests for volunteer oat and wheat control with quizalofop are shown in TABLE 3. The adjuvants Activator 90.RTM, Scoil.RTM, Prime Oil.RTM, Hi-Per-Oil.RTM, Composition 1, and Composition 2 were added to water (concentration based on volume per volume or at pt/A are shown in TABLE 3) with quizalofop at 0.25 oz/A to prepare the final aqueous spray mixture applied at 8.5 gal/A to 3–4-leaf stage wheat and oat. TABLE 3 includes the results of assessment made 2 WAT (weeks after treatment).

Composition 1 and Composition 2 adjuvants of present invention applied at the reduced concentrations of 0.5% and 0.75 pt/A provided equal quizalofop efficacy on volunteer oat and wheat as the reference commercial adjuvants Scoil-.RTM applied at recommended rates of 1% and 1.5 pt/A or petroleum oil Prime Oil.RTM at 2 pt/A and Hi-Per-Oil at 2 pt/A.

TABLE 3

Volunteer oat and wheat control 2 WAT with quizalofop at 0.25 oz/A as influenced by adjuvants, Fargo, ND, field experiment, 2001.

| Adjuvant | Oat | Wheat |
| --- | --- | --- |
| Activator 90.RTM 0.5% | 77 | 86 |
| Scoil.RTM 1% | 81 | 91 |
| Scoil.RTM 1.5 pt/A | 80 | 91 |
| Prime Oil.RTM 2 pt/A | 84 | 94 |
| Hi-Per-Oil 1 pt/A | 86 | 95 |
| Quad 7.RTM 1% | 93 | 96 |
| Composition 1 0.5% | 84 | 93 |
| Composition 1 0.75 pt/A | 85 | 94 |
| Composition 2 0.5% | 88 | 93 |
| Composition 2 0.75 pt/A | 85 | 92 |
| LSD (0.05) | 9 | 6 |

Activator 90.RTM is a nonionic surfactant of alkylpolyoxyethylene ethers and free fatty acids from Loveland Industries. Scoil.RTM is a methylated vegetable oil from AGSCO Inc.; Prime Oil.RTM is petroleum oil from Agriliance; Hi-Per-Oil.RTM is a petroleum oil from Agriliance. Composition 1 is an experimental homogenous adjuvant that refers to the present invention consisting of methylated canola oil (55%), ammonium hydroxide (5%), and Pluronic L 62 block copolymer nonionic surfactant (40%) from BASF Corp. Composition 2 is an experimental homogenous adjuvant that refers to the present invention consisting of methylated canola oil (55%), ammonium hydroxide (5%), Pluronic L 62.RTM block copolymer nonionic surfactant (20%) from BASF Corp., and Tergitol 15-S-9.RTM secondary alcohol ethoxylate surfactant (20%) from Union Carbide Corp.

The results of field test with nicosulfuron plus rimsulfuron plus clopyralid plus flumetsulam (Accent Gold.RTM) are shown in TABLE 4. The adjuvants Activator 90.RTM, Scoil.RTM, Prime Oil.RTM, Hi-Per-Oil.RTM, Composition 1, and Composition 2 were added to water (concentration based on volume per volume or at pt/A are shown in TABLE 3) with nicosulfuron plus rimsulfuron plus clopyralid plus flumetsulam (0.1+0.1+0.9+0.3 oz active ingredient/A) to prepare the final aqueous spray mixture applied at 8.5 gal/A. TABLE 4 includes the results of assessment made 4 WAT (weeks after treatment).

Composition 1 and Composition 2 adjuvants of present invention applied at the reduced concentrations of 0.5% and 0.75 pt/A were equally or more effective than the reference commercial adjuvants Activator 90.RTM, Scoil.RTM, Prime Oil.RTM, and Hi-Per-Oil at recommended concentrations and rates, without enhancing corn injury.

TABLE 4

Yellow foxtail and common lambsquarters control 4 WAT with nicosulfuron plus rimsulfuron plus clopyralid plus flumetsulam at 0.1 + 0.1 + 0.9 + 0.3 oz/A (Accent Gold. RTM) in corn as influenced by adjuvants, Oakes, ND, 2001.

| Adjuvant | Corn | Yellow foxtail | Common lambsquarters |
| --- | --- | --- | --- |
| Activator 90.RTM 0.5% | 6 | 66 | 60 |
| Scoil.RTM 1% | 7 | 80 | 81 |
| Scoil.RTM 1.5 pt/A | 10 | 90 | 89 |
| Prime Oil.RTM 2 pt/A | 9 | 84 | 86 |
| Hi-Per-Oil 1 pt/A | 8 | 89 | 88 |
| Composition 1 0.5% | 10 | 88 | 89 |
| Composition 1 0.75 pt/A | 14 | 88 | 90 |
| Composition 2 0.5% | 11 | 91 | 90 |
| Composition 2 0.75 pt/A | 11 | 90 | 91 |
| LSD (0.05) | NS | 11 | 9 |

Activator 90.RTM is a nonionic surfactant of alkylpolyoxyethylene ethers and free fatty acids from Loveland Industries. Scoil.RTM is a methylated vegetable oil from AGSCO Inc.; Prime Oil.RTM is petroleum oil from Agriliance; Hi-Per-Oil.RTM is a petroleum oil from Agriliance. Composition 1 is an experimental homogenous adjuvant that refers to the present invention consisting of methylated canola oil (55%), ammonium hydroxide (5%), and Pluronic L 62 block copolymer nonionic surfactant (40%) from BASF Corp. Composition 2 is an experimental homogenous adjuvant that refers to the present invention consisting of methylated canola oil (55%), ammonium hydroxide (5%), Pluronic L 62.RTM block copolymer nonionic surfactant (20%) from BASF Corp., and Tergitol 15-S-9.RTM secondary alcohol ethoxylate surfactant (20%) from Union Carbide Corp.

The results of field test with nicosulfuron plus rimsulfuron plus atrazine (Basis Gold.RTM) are shown in TABLE 5. The adjuvants Activator 90.RTM, Scoil.RTM, Prime Oil.RTM, Hi-Per-Oil.RTM, Composition 1, and Composition 2 were added to water (concentrations based on volume per volume or at pt/A are shown in TABLE 5) with nicosulfuron plus rimsulfuron plus clopyralid plus flumetsulam (0.1+0.1+7.6 oz active ingredient/A) to prepare the final aqueous spray mixture applied at 8.5 gal/A. TABLE 5 includes the results of assessment made 8 WAT (weeks after treatment).

Composition 1 and Composition 2 adjuvants of present invention applied at reduced concentrations of 0.5% and 0.75 pt/A were equally or more effective than the reference commercial adjuvants Activator 90.RTM, Scoil.RTM, Prime Oil.RTM, and Hi-Per-Oil at recommended concentrations and rates, without enhancing corn injury.

TABLE 5

Yellow foxtail, common lambsquarters, volunteer flax, and wheat control 6 WAT with nicosulfuron plus rimsulfuron plus atrazine at 0.1 + 0.1 + 7.6 oz/A (Basis Gold.RTM) in corn as influenced by adjuvants, Oakes, ND, 2001.

| Adjuvant | Corn | Yellow foxtail | Common lambs-quarters | Flax | Wheat |
|---|---|---|---|---|---|
| Activator 90.RTM 0.5% | 0 | 63 | 90 | 59 | 68 |
| Scoil.RTM 1% | 0 | 79 | 97 | 75 | 74 |
| Scoil.RTM 1.5 pt/A | 0 | 81 | 99 | 78 | 80 |
| Prime Oil.RTM 2 pt/A | 0 | 75 | 99 | 76 | 75 |
| Hi-Per_Oil 1 pt/A | 0 | 83 | 99 | 78 | 75 |
| Quad 7.RTM 1% | 0 | 58 | 90 | 68 | 75 |
| L-64.11.2.1 1% | 0 | 83 | 96 | 78 | 78 |
| L-64.11.2.1 1.5 pt/A | 0 | 86 | 97 | 84 | 84 |
| Composition 1 0.5% | 0 | 84 | 97 | 75 | 78 |
| Composition 1 0.75 pt/A | 0 | 83 | 99 | 76 | 75 |
| Composition 2 0.5% | 0 | 80 | 93 | 78 | 81 |
| Composition 2 0.75 pt/A | 0 | 91 | 99 | 89 | 89 |
| LSD (0.05) | NS | 12 | 6 | 9 | 10 |

Activator 90.RTM is a nonionic surfactant of alkylpolyoxyethylene ethers and free fatty acids from Loveland Industries. Scoil.RTM is a methylated vegetable oil from AGSCO Inc.; Prime Oil.RTM is petroleum oil from Agriliance; Hi-Per-Oil.RTM is a petroleum oil from Agriliance. Composition 1 is an experimental homogenous adjuvant that refers to the present invention consisting of methylated canola oil (55%), ammonium hydroxide (5%), and Pluronic L 62.RTM block copolymer nonionic surfactant (45%) from BASF Corp. Composition 2 is an experimental homogenous adjuvant which refers to the present invention consisting of methylated canola oil (55%), ammonium hydroxide (5%), Pluronic L 62.RTM block copolymer nonionic surfactant (20%) from BASF Corp., and Tergitol 15-S-9.RTM secondary alcohol ethoxylate surfactant (20%) from Union Carbide Corp.

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A homogenous, clear, continuous, and stable adjuvant blend comprising:
    a petroleum oil;
    a pH adjuster in an amount effective for providing an alkaline pH of above about 7 to about 10 when in a final spray composition; and
    from about 30 to about 70 weight percent of at least one nonionic surfactant based on the weight of the adjuvant blend.

2. The adjuvant blend according to claim 1 wherein the pH adjuster is selected from the group consisting of ammonium hydroxide, potassium hydroxide, sodium hydroxide, triethanolamine, primary amino alcohols, and mixtures thereof.

3. The adjuvant blend according to claim 1 wherein the nonionic surfactant is selected from the group consisting of linear alcohol ethoxylates, secondary alcohol ethoxylates, block copolymers of ethylene and propylene oxide, and mixtures thereof.

4. The adjuvant blend according to claim 1 wherein the adjuvant blend contains from about 30 to about 70 weight percent petroleum oil, based on the weight of the adjuvant blend.

5. The adjuvant blend according to claim 1 further comprising from about 1 to about 69 weight percent, based on the weight of the adjuvant blend, of a second oil selected from the group consisting of vegetable oils, methylated, ethylated and butylated seed oil, fatty acids, partially saponified fatty acids, and mixtures thereof.

6. A homogeneous, clear, and continuous, and stable adjuvant blend comprising:
    an oil selected from the group consisting of petroleum oil, vegetable oils, methylated, ethylated and butylated seed oil, fatty acids, partially saponified fatty acids, and mixtures thereof;
    a pH adjuster in an amount effective for providing an alkaline pH of above about 7 to about 10 when in a final spray composition; and
    from about 30 to 70 weight percent of at least one nonionic surfactant, based on the weight of the adjuvant blend.

7. The adjuvant blend according to claim 6 wherein the pH adjuster is selected from the group consisting of ammonium hydroxide, potassium hydroxide, sodium hydroxide, triethanolamine, primary amino alcohols, and mixtures thereof.

8. The adjuvant blend according to claim 6 wherein the nonionic surfactant is selected from the group consisting of linear alcohol ethoxylates, secondary alcohol ethoxylates, block copolymers of ethylene and propylene oxide, and mixtures thereof.

9. The adjuvant blend according to claim 6 wherein the adjuvant blend contains from about 30 to about 70 weight percent oil, based on the weight of the adjuvant blend.

10. A homogenous, clear, continuous, and stable adjuvant blend comprising:
    from about 30 to about 70 weight percent, based on the weight of the adjuvant blend, of a petroleum oil;
    a pH adjuster in an amount effective for providing an alkaline pH of above about 7 to about 10 when in a final spray composition; and
    from about 30 to about 70 weight percent, based on the weight of the adjuvant blend, of at least one nonionic surfactant.

11. The adjuvant blend according to claim 10 wherein the pH adjuster is selected from the group consisting of ammonium hydroxide, potassium hydroxide, sodium hydroxide, triethanolamine, primary amino alcohols, and mixtures thereof.

12. The adjuvant blend according to claim 10 wherein the nonionic surfactant is selected from the group consisting of linear alcohol ethoxylates, secondary alcohol ethoxylates, block copolymers of ethylene and propylene oxide, and mixtures thereof.

13. The adjuvant blend according to claim 10 further comprising from about 1 to about 69 weight percent, based on the weight of the adjuvant blend, of a second oil selected from the group consisting of vegetable oils, methylated, ethylated and butylated seed oil, fatty acids, partially saponified fatty acids, and mixtures thereof.

14. A homogenous, clear, continuous, and stable adjuvant blend comprising:
   a methylated, ethylated or butylated seed oil, or mixtures thereof;
   a pH adjuster in an amount effective for providing an alkaline pH of above about 7 to about 10 when in a final spray composition; and
   from about 30 to about 70 weight percent of at least one nonionic surfactant based on the weight of the adjuvant blend.

15. A homogenous, clear, continuous, and stable adjuvant blend comprising:
   a petroleum oil;
   a pH adjuster in an amount effective for providing an alkaline pH of above about 7 to about 10 when in a final spray composition; and
   from about 30 to about 70 weight percent of at least one nonionic surfactant based on the weight of the adjuvant blend, wherein the blend does not include added water.

16. A method of controlling weeds which comprises applying a postemergence herbicidal spray composition to weeds and/or other undesired vegetation, the herbicidal spray composition comprising from about 0.5 to about 1 weight percent, based on the weight of the spray composition, of an adjuvant blend, an effective amount of a postemergence herbicide, and water to make up the final spray composition, the adjuvant blend comprising:
   a petroleum oil;
   a pH adjuster in an amount effective for providing an alkaline pH of above about 7 to about 10 when in a final spray composition; and
   at least one nonionic surfactant.

17. The method of controlling weeds according to claim 16 wherein the pH adjuster is selected from the group consisting of ammonium hydroxide, potassium hydroxide, sodium hydroxide, triethanolamine, primary amino alcohols, and mixtures thereof.

18. The method of controlling weeds according to claim 16 wherein the nonionic surfactant is selected from the group consisting of linear alcohol ethoxylates, secondary alcohol ethoxylates, block copolymers of ethylene and propylene oxide, and mixtures thereof.

19. The method of controlling weeds according to claim 16 wherein the adjuvant blend contains from about 30 to about 70 weight percent nonionic surfactant, based on the weight of the adjuvant blend.

20. The method of controlling weeds according to claim 16 further comprising from about 1 to about 69 weight percent, based on the weight of the adjuvant blend, of a second oil selected from the group consisting of vegetable oils, methylated, ethylated and butylated seed oil, fatty acids, partially saponified fatty acids, and mixtures thereof.

21. The method of controlling weeds according to claim 16 wherein the herbicide is selected from the group consisting of nicosulfuron, foramsulfuron, primisulfuron, mesosulfuron, mesotrione, rimsulfuron, imazethapyr, flucarbazone, quizalofop, clethodim, atrazine and mixtures thereof.

22. The method of controlling weeds according to claim 16 wherein the herbicidal spray composition includes from about 0.001 to about 4 weight percent herbicide, based on the weight of the herbicidal spray composition.

23. A postemergence herbicidal aqueous spray composition comprising from about 0.5 to about 1 weight percent, based on the weight of the spray composition, of an adjuvant blend, an effective amount of a postemergence herbicide, and water to make up the final spray composition, the adjuvant blend comprising:
   a petroleum oil;
   a pH adjuster in an amount effective for providing an alkaline pH of above about 7 to about 10 when in a final spray composition; and
   at least one nonionic surfactant.

24. The postemergence herbicidal aqueous spray composition according to claim 23 wherein the pH adjuster is selected from the group consisting of ammonium hydroxide, potassium hydroxide, sodium hydroxide, triethanolamine, primary amino alcohols, and mixtures thereof.

25. The postemergence herbicidal aqueous spray composition according to claim 23 wherein the nonionic surfactant is selected from the group consisting of linear alcohol ethoxylates, secondary alcohol ethoxylates, block copolymers of ethylene and propylene oxide, and mixtures thereof.

26. The postemergence herbicidal aqueous spray composition according to claim 23 wherein the adjuvant blend contains from about 30 to about 70 weight percent petroleum oil, based on the weight of the adjuvant blend.

27. The postemergence herbicidal aqueous spray composition according to claim 23 wherein the adjuvant blend contains from about 30 to about 70 weight percent nonionic surfactant, based on the weight of the adjuvant blend.

28. The postemergence herbicidal aqueous spray composition according to claim 23 further comprising from about 1 to about 69 weight percent, based on the weight of the adjuvant blend, of a second oil selected from the group consisting of vegetable oils, methylated, ethylated and butylated seed oil, fatty acids, partially saponified fatty acids, and mixtures thereof.

29. The postemergence herbicidal aqueous spray composition according to claim 23 wherein the herbicide is selected from the group consisting of nicosulfuron, foramsulfuron, primisulfuron, mesosulfuron, mesotrione, rimsulfuron, imazethapyr, flucarbazone, quizalofop, clethodim, atrazine and mixtures thereof.

30. The postemergence herbicidal aqueous spray composition according to claim 23 wherein the herbicidal spray composition includes from about 0.001 to about 4 weight percent herbicide, based on the weight of the herbicidal spray composition.

* * * * *